(12) United States Patent
Alonso Cohen et al.

(10) Patent No.: US 12,178,844 B2
(45) Date of Patent: Dec. 31, 2024

(54) COMPOSITIONS FOR TREATING AUTOIMMUNE ARTHRITIS

(71) Applicant: DEVINTEC SAGL, Lugano (CH)

(72) Inventors: Miguel Angel Alonso Cohen, Herreros De Jamuz (ES); Rossana Sidoti, Como (IT); Bhavna Karnani, Varese (IT)

(73) Assignee: DEVINTEC SAGL, Lugano (CH)

( * ) Notice: Subject to any disclaimer, the term of this patent is extended or adjusted under 35 U.S.C. 154(b) by 0 days.

(21) Appl. No.: 18/317,277

(22) Filed: May 15, 2023

(65) Prior Publication Data

US 2024/0091308 A1    Mar. 21, 2024

Related U.S. Application Data

(63) Continuation of application No. PCT/EP2022/085599, filed on Dec. 13, 2022.

(30) Foreign Application Priority Data

Dec. 14, 2021 (EP) ..................... 21214238

(51) Int. Cl.
*A61K 38/16* (2006.01)
*A61K 31/573* (2006.01)
*A61K 47/36* (2006.01)
*A61P 19/02* (2006.01)

(52) U.S. Cl.
CPC .......... *A61K 38/168* (2013.01); *A61K 31/573* (2013.01); *A61K 47/36* (2013.01); *A61P 19/02* (2018.01)

(58) Field of Classification Search
CPC .... A61K 38/168; A61K 31/573; A61K 47/36; A61P 19/02
See application file for complete search history.

(56) References Cited

U.S. PATENT DOCUMENTS 10,130,601 B2 * 11/2018 Mathisen ............. A61K 36/185

FOREIGN PATENT DOCUMENTS

WO    2017/207223 A1    12/2017
WO    2018/167131 A1     9/2018

OTHER PUBLICATIONS

Lim et al., Bull. Rheum. Dis., 2001, 50(12):1-4 (Abstract).*
Abe et al., Int. J. Tissue React., 2004, vol. 26(3-4):65-73 (Abstract).*
Kamal et al., Int. J. Rheumatol., 2018, vol. 2018, Article ID 4197537, 6 pages.*
Abe et al., "Effects of alpha-linked galactooligosaccharide on adjuvant-induced arthritis in Wistar rats and type II collagen-induced arthritis in DBA/1J mice.", Database Medline [Online], US National Library of Medicine (NLM), Bethesda, MD, US; 2004 (2004); XP002806703; Database accession No. NLM15648438; Abstract.
Balkrishna et al., "Herbo-mineral formulation 'Ashwashila' attenuates rheumatoid arthritis symptoms in collagen-antibody-induced arthritis (CAIA) mice model" Sci Rep., 2019; vol. 9(1); pp. 8025.
Benjamin et al., "Disease Modifying Anti-Rheumatic Drugs (DMARD)" StatPearls, 2021.
Campolo et al., "Effect of a Product Containing Xyloglucan and Pea Protein on a Murine Model of Atopic Dermatitis", International Journal of Molecular Sciences, vol. 21, No. 10, May 19, 2020 (May 19, 2020), p. 3596; XP055927576; DOI: 10.3390/ijms21103596. Retrieved from the Internet: URL:https://www.ncbi.nlm.nih.gov/pmc/articles/PMC279434/pdf/ijms-21-03596.pdf.
Djouzi et al., "Compared effects of three oligosaccharides on metabolism of intestinal microflora in rats inoculated with a human faecal flora", British Journal of Nutrition, vol. 78, No. 2, Jan. 1, 1997 (Jan. 1, 1997), pp. 313-324, XP002516708, ISSN: 0007-1145, DOI: 10.1079/BJN19970149.
Dürholz et al., "Dietary Short-Term Fiber Interventions in Arthritis Patients Increase Systemic SCFA Levels and Regulate Inflammation", Nutrients, vol. 12, No. 10, Oct. 20, 2020 (Oct. 20, 2020), p. 3207, XP55928087, DOI: 10.3390/nu12103207. Retrieved from the Internet: URL:https://www.ncbi.nlm.nih.gov/pmc/articles/PMC7589100/pdf/nutrients-12-03207.pdf.
Jia et al., "A novel dexamethasone-loaded liposome alleviates rheumatoid arthritis in rats"; International Journal of Pharmaceutics; 2018; vol. 540 (1-2); pp. 57-64.
Joosten et al., "Synergistic protection against cartilage destruction by low dose prednisolone and interleukin-10 in established murine collagen arthritis". Inflamm. res. 48, 48-55, 1999.
Kamal et al., "Gum Arabic Fibers Decreased Inflammatory Markers and Disease Severity Score among Rheumatoid Arthritis Patients, Phase II Trial", International Journal of Rheumatology, vol. 2018, Jul. 5, 2018 (Jul. 5, 2018), pp. 1-6, XP55928086, ISSN: 1687-9260, DOI: 10.1155/2018/4197537. Retrieved from the Internet: URL:https://www.ncbi.nlm.nih.gov/pmc/articles/PMC6077585/pdf/IJR2018-4197537.pdf.
Martinsson et al., "Higher serum levels of short-chain fatty acids are associated with non-progression to arthritis in individuals at increased risk of RA", Ann Rheum Dis March, vol. 81, No. 3, Nov. 24, 2021 (Nov. 24, 2021), pp. 445-447, XP55928089. Retrieved from the Internet: URL:https://ard.bmj.com /content/annrheumdis/81/3/445.full.pdf.

(Continued)

*Primary Examiner* — Xiaozhen Xie
(74) *Attorney, Agent, or Firm* — Chrisman Gallo Tochtrop LLC

(57) ABSTRACT

The present invention provides pea protein and compositions comprising pea protein for use in the prevention and/or treatment of autoimmune arthritis. The invention also provides said compositions for use in combination therapy with an antirheumatic drug. The invention also provides compositions comprising pea protein, alpha-glucooligosaccharide, acacia gum, and an antirheumatic drug, and their use as a medicament. The compositions of the invention are particularly useful for treating rheumatoid arthritis.

18 Claims, 11 Drawing Sheets
Specification includes a Sequence Listing.

(56) References Cited

OTHER PUBLICATIONS

Rashidan et al., "Detection of B. fragilis group and diversity of bft enterotoxin and antibiotic resistance markers cepA, cfiA and nim among intestinal Bacteroides fragilis strains in patients with inflammatory bowel disease"; Anaerobe; 2018; vol. 50:93; pp. 100.

Rosser et al., "Microbiota-Derived Metabolites Suppress Arthritis by Amplifying Aryl-Hydrocarbon Receptor Activation in Regulatory B Cells", Cell Metabolism, Cell Press, United States, vol. 31, No. 4, Mar. 25, 2020 (Mar. 25, 2020), p. 837, XP086124131, ISSN: 1550-4131, DOI: 10.1016/J.CMET.2020.03.003 [retrieved on Mar. 25, 2020].

Terato et al., "Induction of arthritis with monoclonal antibodies to collagen" J. Immunol., 1992, vol. 148(7), pp. 2103-2108.

Dominika et al., "The study on the impact of glycated pea proteins on human intestinal bacteria", International Journal of Food Microbiology, Elsevier BV, NL, vol. 145, No. 1, Jan. 2, 2011 (Jan. 2, 2011), pp. 267-272. XP028144820, ISSN: 0168-1605. DOI: 10.1016/J.IJFOODMICRO.2011.01.002 [retrieved on Jan. 8, 2011].

International Search Report and Written Opinion of International Application No. PCT/EP2022/085599, dated Mar. 16, 2023, 16 pages.

\* cited by examiner

A

B

C

```
                            SEQUENCE LISTING

Sequence total quantity: 6
SEQ ID NO: 1            moltype = DNA  length = 20
FEATURE                 Location/Qualifiers
source                  1..20
                        mol_type = other DNA
                        organism = synthetic construct
SEQUENCE: 1
tgattccgca tggtttcatt                                                    20

SEQ ID NO: 2            moltype = DNA  length = 20
FEATURE                 Location/Qualifiers
source                  1..20
                        mol_type = other DNA
                        organism = synthetic construct
SEQUENCE: 2
cgacccatag agccttcatc                                                    20

SEQ ID NO: 3            moltype = DNA  length = 16
FEATURE                 Location/Qualifiers
source                  1..16
                        mol_type = other DNA
                        organism = synthetic construct
SEQUENCE: 3
cccgacggga ggggat                                                        16

SEQ ID NO: 4            moltype = DNA  length = 22
FEATURE                 Location/Qualifiers
source                  1..22
                        mol_type = other DNA
                        organism = synthetic construct
SEQUENCE: 4
cttctgcagg tacagtcttg ac                                                 22

SEQ ID NO: 5            moltype = DNA  length = 17
FEATURE                 Location/Qualifiers
source                  1..17
                        mol_type = other DNA
                        organism = synthetic construct
SEQUENCE: 5
cagcagccgc ggtaata                                                       17

SEQ ID NO: 6            moltype = DNA  length = 19
FEATURE                 Location/Qualifiers
source                  1..19
                        mol_type = other DNA
                        organism = synthetic construct
SEQUENCE: 6
ggcatccatc gtttaccgt                                                     19
```

COMPOSITIONS FOR TREATING AUTOIMMUNE ARTHRITIS

This application is a continuation of PCT international application PCT/EP2022/085599, filed on Dec. 13, 2022, which claims priority of European Patent Application EP21214238, filed on Dec. 14, 2021, both of which are incorporated herein by reference in their entirety.

SEQUENCE LISTING

The material in the xml file, named P5914PC00-sequence-listing-20221221.xml, created Sep. 13, 2023, file size of 6,112 bytes, is hereby incorporated by reference.

TECHNICAL FIELD

The present invention belongs to the field of medicine, in particular, to the field of compositions for preventing or treating autoimmune arthritis. The compositions of the invention are particularly useful in combination therapy with antirheumatic drugs for treating rheumatoid arthritis.

BACKGROUND ART

Autoimmune arthritis are a group of autoimmune-associated diseases in which the patient's own immune system attacks the joints and causes inflammation. Rheumatoid arthritis (RA) is the most common autoimmune rheumatic disease. RA affects one percent of the world's population. It is characterized by synovial inflammation of joints, which can lead to progressive erosion of bone, irreversible damage to the joint, loss of function, and resultant disability. RA can develop at any age, but incidence increases with age, peaking in the fifth decade. The incidence of RA is two to three times higher in women.

The etiology of RA is incompletely understood, but multiple environmental and genetic factors seem to contribute to the development of the disease. Obesity, smoking, and nulliparity increase the risk. Other environmental risk factors associated with RA, although not well understood, include low socioeconomic status and viral and bacterial infections, including those caused by periodontal and lung pathogens. Rates of RA development are higher in monozygotic twins, implicating genetics as a contributing factor. Genome-wide association studies have characterized more than 100 loci associated with RA risk; most involve immune mechanisms.

As a result of the unknown RA etiology, there is an absence of effective causal treatments currently in the clinic. In general, the available treatments aim to control pain and inflammation and, ultimately, slow the progression of joint destruction and disability.

Symptomatic RA treatments mainly involve the administration of analgesics to reduce pain, non-steroidal anti-inflammatory drugs (NSAIDs) as well as corticosteroids to reduce inflammation. However, chronic administration of these drugs damages the stomach, liver and kidneys, among other organs. In addition, their effectiveness decreases over time requiring increased doses or the use of more aggressive drugs which often leads to more severe side effects. Furthermore, the chronic use of corticosteroids has been shown to induce bone fragility, neuropsychiatric effects, muscle wasting and a reduction in immunity, leaving the patient vulnerable to infections.

Disease-modifying antirheumatic drugs (DMARDs) are the cornerstone of RA treatment throughout all stages of the disease, which aim to maintain or improve physical function and retard radiographic joint damage. These most often include the administration of methotrexate, an anticancer drug successfully used to prevent and reduce the number of inflammatory flares. However, this drug includes many side effects such as fever, anemia, respiratory problems, teratogenic risks and bone marrow toxicity, among other risks. Therefore, it is not well tolerated by all patients. Other medicines used in place of or in conjunction with methotrexate, are certain antimalarials and inhibitors of TNF, a protein involved in inflammatory processes. However, none of these drugs are free from side effects. In particular, there is a risk of weakening the immune system, as well as high toxicity on the patient's vital organs such as the liver and kidney. More recently, biological compounds, such as antibodies—that target TNFα, B-cells, or T-cells—have been used to treat RA. However, these biologics are very costly and many patients fail to respond to them.

Thus, in spite of the efforts made so far, there is still the need for compositions with improved efficacy and less secondary effects for treating and preventing autoimmune arthritis, in particular RA.

SUMMARY OF INVENTION

The present inventors have developed new compositions based on natural products for preventing and treating autoimmune arthritis, in particular RA.

Seeking natural products that could help in the treatment or prevention of autoimmune arthritis without causing unwanted secondary effects, the present inventors surprisingly found through extensive experimentation that compositions comprising pea protein are capable of suppressing bone resorption, reducing bone erosion and cartilage destruction in the joints in a collagen antibody-induced arthritis (CAIA) mouse model of RA (see Tables 1-4, groups 17, 19, 21 vs group 9).

Strikingly, the therapeutic anti-RA efficiency of the composition comprising pea protein was equivalent—and sometimes even higher—than prednisolone at high concentration (1 mg/kg), a corticosteroid commonly used for treating RA which is associated with several side effects that currently hinder its chronic application (see Tables 3-4, group 21 vs group 14).

Therefore, the composition of the invention for treating autoimmune arthritis has several advantages over the prior art. First of all, pea protein is widely available and inexpensive, as opposed to many antirheumatic drugs, particularly the newly developed biological drugs; secondly, the composition is based on safe natural products known to be well tolerated and secure for human consumption, thereby reducing the risk of undesired effects after long-term administration; and finally, the composition of the invention can be used in combination with other anti-RA treatments with surprising synergistic results, as shown in the examples below (see FIGS. 1-11, groups 13, 15 vs 12, 14), thereby providing improved combination therapies with lower side effects.

In conclusion, the results herein provided reveal that compositions comprising pea protein are useful for preventing and treating autoimmune arthritis, in particular RA.

Without wishing to be bound by any theory, the present inventors believe that the therapeutic efficacy of the composition of the invention is based on a new molecular mechanism in which the composition would act as a mucomimetic agent in the gastrointestinal tract that blocks the contact of the intestinal intraepithelial lymphocytes with the antigens of the lumen, thereby reducing the general inflammatory state of the organism.

Thus, in a first aspect, the invention provides pea protein for use in the prevention and/or treatment of autoimmune arthritis.

This aspect can also be formulated as the use of pea protein for the manufacture of a medicament for the treatment or prevention of autoimmune arthritis. This aspect can also be formulated as a method for treating or preventing autoimmune arthritis, the method comprising administering a therapeutically effective amount of pea protein together with pharmaceutically acceptable excipients or carriers to a subject in need thereof.

In a second aspect, the invention provides a composition comprising pea protein for use in the prevention and/or treatment of autoimmune arthritis.

This aspect can also be formulated as the use of a composition of the invention for the manufacture of a medicament for the treatment or prevention of autoimmune arthritis. This aspect can also be formulated as a method for treating or preventing autoimmune arthritis, the method comprising administering a therapeutically effective amount of the composition of the invention together with pharmaceutically acceptable excipients or carriers to a subject in need thereof.

The inventors also surprisingly found that even better therapeutic results were obtained when pea protein was further combined with alpha-glucooligosaccharide and acacia gum, together with an antirheumatic drug. As shown in the examples below, this particular combination provides a synergistic therapeutic effect on RA treatment as shown in the significant recovery of the microbial compositions of mice treated with said combination (FIGS. 9 and 11, group 16 vs group 9).

Thus, in a third aspect, the invention provides a composition comprising pea protein, alpha-glucooligosaccharide, acacia gum, and antirheumatic drug.

In a fourth aspect, the invention provides a pharmaceutical composition comprising a therapeutically effective amount of pea protein, alpha-glucooligosaccharide, acacia gum, and antirheumatic drug, with at least one pharmaceutically acceptable excipient or carrier.

In a fifth aspect, the invention provides the composition as defined in the third aspect, or the pharmaceutical composition as defined in the fourth aspect for use as a medicament.

DETAILED DESCRIPTION OF THE INVENTION

Figure 1:
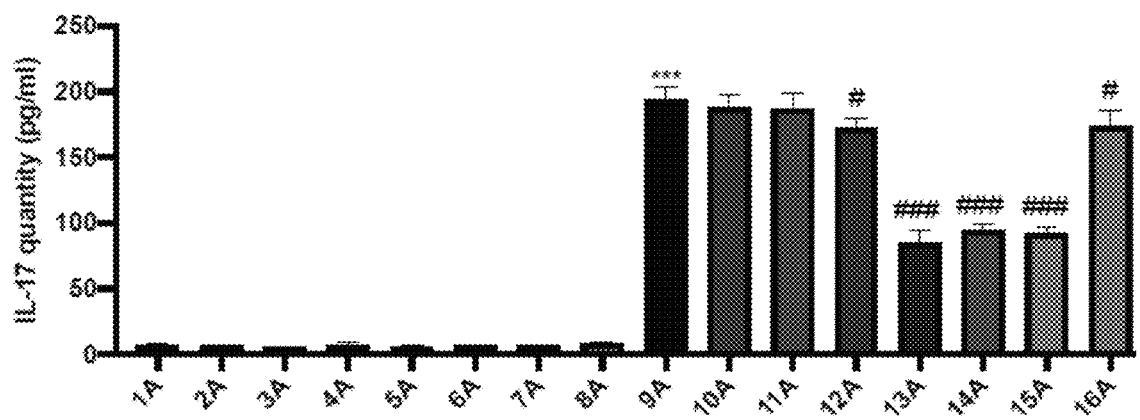
FIG. 1 shows the evaluation of cytokine in arthritic hind paws of mice from group A. Values are indicated as the mean±SEM. ***P<0.001 vs sham (1A); ###P<0.001, ##P<0.01 and #p<0.005 vs CAIA (9A).
Figure 1:
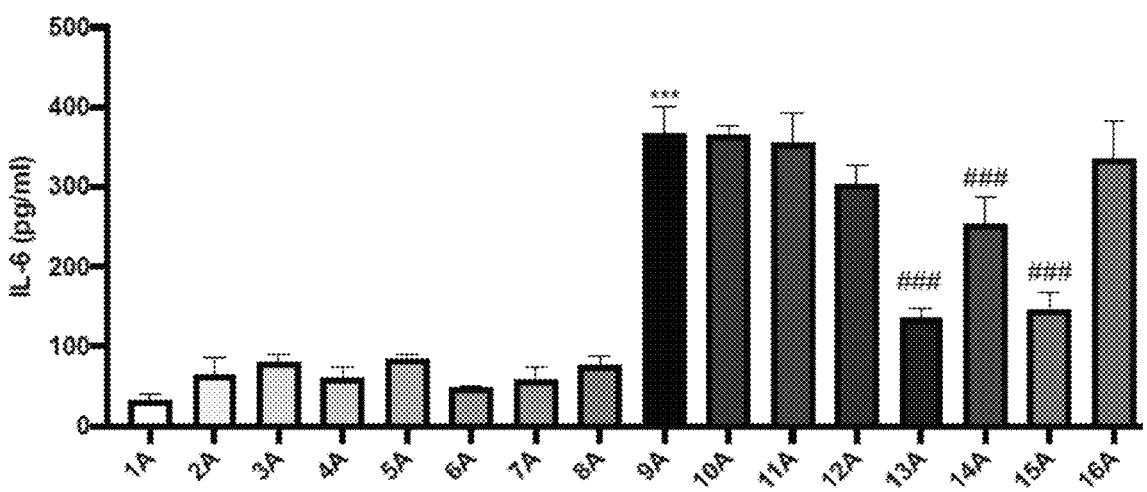
Figure 1:
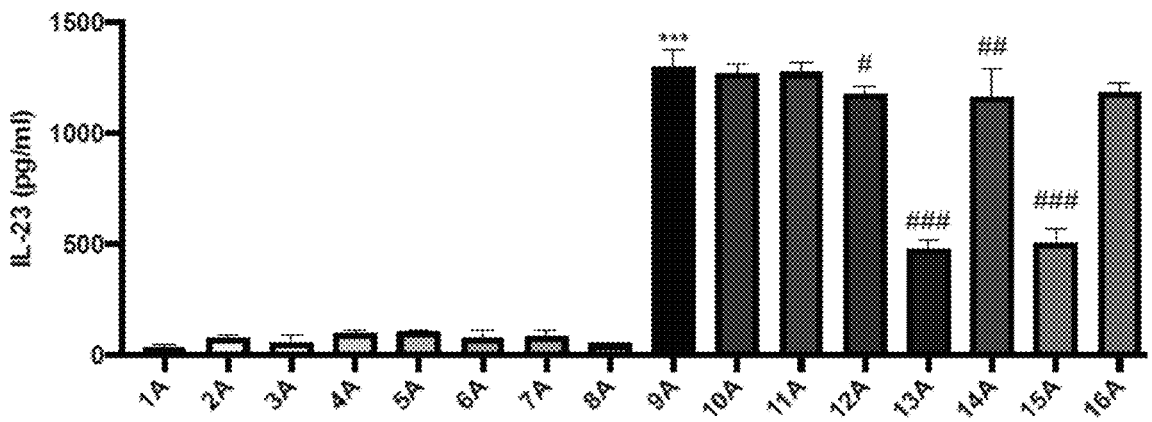
Figure 1:
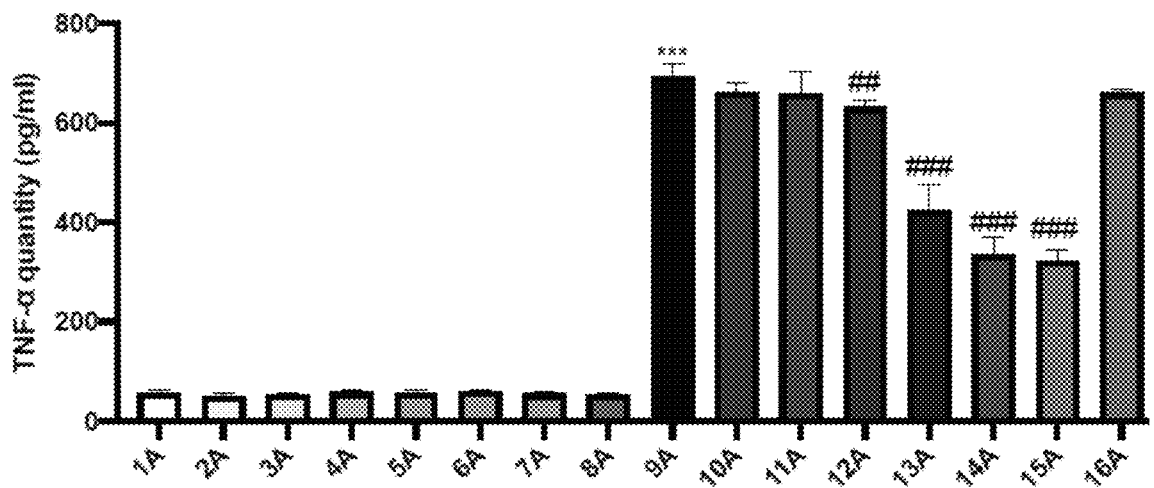
Figure 1:
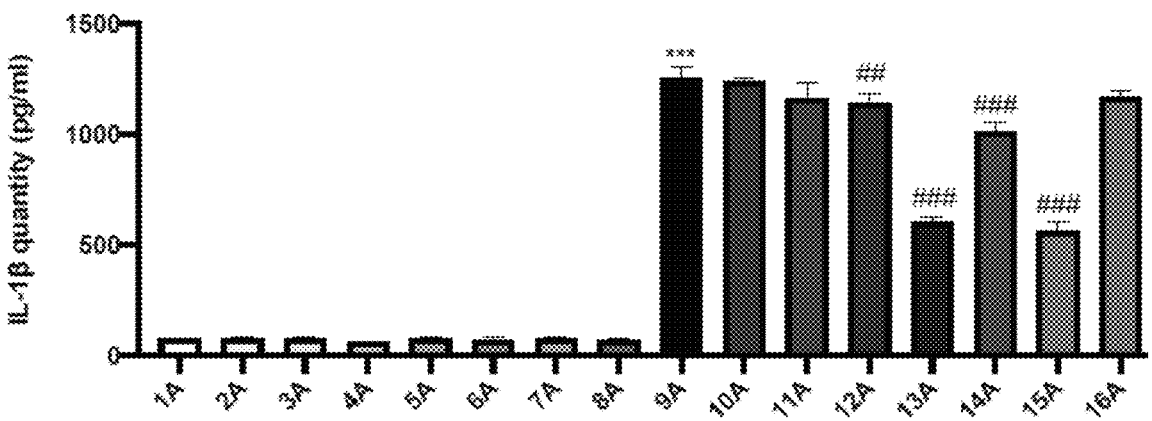

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For purposes of the present invention, any ranges given include both the lower and the upper end-points of the range. Ranges given, such as concentrations and the like, should be considered approximate, unless specifically stated.

As used herein, the indefinite articles "a" and "an" are synonymous with "at least one" or "one or more." Unless indicated otherwise, definite articles used herein, such as "the" also include the plural of the noun.

As above disclosed, the present invention provides a pea protein and a composition comprising pea protein for use in the prevention and/or treatment of rheumatoid arthritis.

In the present invention, the term "pea protein" is the generic name given to any protein isolate obtained from yellow pea, *Pisum sativum*, seeds. "Pea protein" contains Legumin, which has some similar properties to Casein, and pea protein products are promoted as an alternative to whey protein. "Pea protein" is worldwide sold under different trademarks such as, Nutralys®, and P80X, among others. And it can also be prepared from pea cultivars by well-known routine methods, such as alkali extraction/isoelectric precipitation (AE-IP), salt extraction-dialysis (SE), and micellar precipitation (MP), among others. Pea protein can be commercially obtained (CAS number 222400-29-5) (Pisane® F9).

As used herein, "autoimmune arthritis" refers a group of autoimmune-associated diseases that share a sustained chronic inflammation of the joints that eventually result in joint pain, stiffness, and mobility problems. In a particular embodiment of the first and second aspects, optionally in combination with any of the embodiments provided above or below, the autoimmune arthritis is selected form the group consisting of rheumatoid arthritis, psoriatic arthritis, ankylosing spondylitis, and juvenile idiopathic arthritis. In an even more particular embodiment, the autoimmune arthritis is rheumatoid arthritis.

The term "rheumatoid arthritis" or "RA" refers to a chronic autoimmune disease characterized primarily by persistent synovitis and progressive destruction of cartilage and bone in multiple joints. The hallmark of RA is a symmetric polyarthritis characteristically involving the small joints of the hands and feet. The inflammatory process can also target other organs, characteristically bone marrow (anemia), eye (scleritis, episcleritis), lung (interstitial pneumonitis, pleuritis), cardiac (pericarditis) and skin (nodules, leukocytoclastic vasculitis).

The term "treating", "to treat" or "treatment", include without limitation restraining, slowing, stopping, reducing, ameliorating, or reversing the progression or severity of an existing symptom, clinical sign, disorder, condition, or disease. A treatment may be applied or administered therapeutically.

The term "preventing", "to prevent" or "prevention", include without limitation decreasing, reducing or ameliorating the risk of a symptom, clinical sings, disorder, condition, or disease, and protecting a subject from a symptom, clinical signs, disorder, condition, or disease. A prevention may be applied or administered prophylactically.

In one embodiment of the second aspect of the invention, optionally in combination with one or more of the embodiments described above or below, the composition comprises pea protein at a concentration from 1% w/w to 100% w/w, from 10% w/w to 80% w/w, from 20% w/w to 60% w/w, from 30% w/w to 50% w/w, or from 35% w/w to 45% w/w. In an even more particular embodiment, the composition comprises 41.18% w/w of pea protein.

As used herein, "% by weight" or "% w/w" or "% wt" of a component refers to the amount of the single component relative to the total weight of the composition or, if specifically mentioned, of another component.

In one embodiment of the second aspect of the invention, optionally in combination with one or more of the embodiments described above or below, the prevention or treatment comprises administering to a subject a dosage unit of the composition comprising from 10 mg to 500 mg, from 50 mg to 400 mg, from 80 mg to 300 mg, from 100 mg to 200 mg, from 120 mg to 160 mg, or from 135 mg to 145 mg, of pea protein per day. In a more particular embodiment, the dosage unit of the composition comprises 140 mg of pea protein per day.

The term "dosage unit" refers to a pharmaceutical or nutraceutical entity that comprises a pharmacologically active ingredient and pharmaceutical or nutraceutical acceptable excipients or carriers and which is actually to be administered to, or to be taken by, a human. The term "dosage unit" also encompasses non-reusable packaging as well, especially when pharmaceutical composition is individually packaged. Further, the "dosage unit" of the invention can be obtained from a larger dosage unit prepared in advanced. These larger dosage units are known as "multi-dose dosage units".

The inventors surprisingly found that when alpha-glucooligosaccharide and acacia gum were added to the composition even better therapeutic results were obtained.

Thus, in an embodiment of the second aspect of the invention, optionally in combination with one or more of the embodments described above or below, the composition further comprises a gum, preferably xanthan gum, tragacanth gum, guar gum, acacia gum, arabic gum, and/or an oligosaccharide, preferably a glucooligosaccharide or a galactooligosaccharide. In a more particular embodiment, the composition further comprises acacia gum and/or alpha-glucooligosaccharide. In a more particular embodiment, the composition comprises pea protein, acacia gum and alpha-glucooligosaccharide. In an even more particular embodiment, the composition consists on pea protein, acacia gum and alpha-glucooligosaccharide.

The terms "acacia gum" or "gum arabic" are used interchangeably and refer to a highly branched, high molecular weight molecule comprised of galactose, arabinose, rhamnose, and glucuronic acid units obtained from acacia secretions. More specifically, the acacia gum is obtained from the bark of an Acacia senegal or its related plants. Generally, it has an average molecular weight between 300 and 800 kDa. It is a commercially obtainable natural substance, which is registered as E-414 or CAS 9000-01-05.

The term "alpha-glucooligosaccharide" or "α-GOS" or "α-GIOS" refers to saccharide polymers formed by glucose monomers joined by α-1,2 and α-1,6 glycosidic linkages. These compounds are commercially available. In a particular embodiment, the α-GOS contains over 80% of long-chain polymers with degree of polymerization greater than 3. In an even more particular embodiment, the α-GOS is BioEcolians®.

In one embodiment of the second aspect of the invention, optionally in combination with one or more of the embodiments described above or below, the composition comprises pea protein and alpha-glucooligosaccharide at a weight ratio (weight/weight) from 1.4:0.1 to 1.4:10, from 1.4:0.5 to 1.4:5, from 1.4:0.8 to 1.4:2, or from 1.4:0.9 to 1.4:1.1. In a more particular embodiment, the composition comprises pea protein and alpha-glucooligosaccharide at a weight ratio 1.4:1.

The term "weight ratio" refers to the relation of weights of the components indicated to treat and/or prevent autoimmune arthritis.

In one embodiment of the second aspect of the invention, optionally in combination with one or more of the embodiments described above or below, the composition comprises pea protein and acacia gum at a weight ratio from 1.4:0.1 to 1.4:10, from 1.4:0.5 to 1.4:5, from 1.4:0.8 to 1.4:2, or from 1.4:0.9 to 1.4:1.1. In a more particular embodiment, the composition comprises pea protein and acacia gum at a weight ratio 1.4:1.

In one embodiment of the second aspect of the invention, optionally in combination with one or more of the embodiments described above or below, the composition comprises pea protein, alpha-glucooligosaccharide, and acacia gum at a weight ratio (weight/weight/weight) from 1.4:0.1:0.1 to 1.4:10:10, from 1.4:0.5:0.5 to 1.4:2:2, from 1.4:0.8:0.8 to 1.4:1.5:1.5, or from 1.4:0.9:0.9 to 1.4:1.1:1.1. In a more particular embodiment, the composition comprises pea protein and acacia gum at a weight ratio 1.4:1:1.

In one embodiment of the second aspect of the invention, optionally in combination with one or more of the embodiments described above or below, the composition further comprises from 1% w/w to 99% w/w, from 10% w/w to 80% w/w, or from 20% w/w to 40% w/w, of alpha-glucooligosaccharide, provided that the sum of the components does not exceed 100%. In a more particular embodiment, the composition comprises 29.41% w/w of alpha-glucooligosaccharide.

In one embodiment of the second aspect of the invention, optionally in combination with one or more of the embodiments described above or below, the composition further comprises from 1% w/w to 100% w/w, from 10% w/w to 80% w/w, or from 20% w/w to 40% w/w, of acacia gum, provided that the sum of the components does not exceed 100%. In a more particular embodiment, the composition comprises 29.41% w/w of acacia gum.

In one embodiment of the second aspect of the invention, optionally in combination with one or more of the embodiments described above or below, the composition comprises from 30% w/w to 50% w/w of pea protein, from 20% w/w to 40% w/w of alpha-glucooligosaccharide; and from 20% w/w to 40% w/w of acacia gum, provided that the sum does not exceed 100%. In a more particular embodiment, the composition comprises 41.18% w/w of pea protein, 29.41% w/w of alpha-glucooligosaccharide; and 29.41% w/w of acacia gum.

In one embodiment of the second aspect of the invention, optionally in combination with one or more of the embodiments described above or below, the prevention or treatment comprises administering to a subject a dosage unit of the composition comprising from 10 mg to 500 mg, from 50 mg to 400 mg, from 80 mg to 300 mg, from 100 mg to 200 mg, from 120 mg to 160 mg, or from 135 mg to 145 mg, of pea protein; from 5 mg to 500 mg, from 10 mg to 400 mg, from 50 mg to 200 mg, from 80 mg to 120 mg, or from 90 mg to 110 mg, of alpha-glucooligosaccharide; and/or from 5 mg to 500 mg, from 10 mg to 400 mg, from 50 mg to 200 mg, from 80 mg to 120 mg, or from 90 mg to 110 mg, of acacia gum per day.

In an even more particular embodiment of the second aspect of the invention, optionally in combination with one or more of the embodiments described above or below, the prevention or treatment comprises administering to a subject a dosage unit of the composition comprising from 100 mg to 200 mg of pea protein, from 50 to 150 mg of alpha-glucooligosaccharide, and from 50 to 150 mg of acacia gum per day. In a more particular embodiment, the prevention or treatment comprises administering to a subject a dosage unit of the composition comprising 140 mg of pea protein, 100 mg of alpha-glucooligosaccharide, and/or 100 mg of acacia gum per day.

As shown in the examples below, the present inventors have also shown that combining pea protein, acacia gum and alpha-glucooligosaccharide together with an antirheumatic drug a synergistic therapeutic effect on the treatment of autoimmune arthritis is provided (see FIGS. 5-10). This allows reducing the therapeutic dose of antirheumatic drug used, thereby reducing its side effects while improving treatment efficacy.

Thus, in one embodiment of the second aspect of the invention, optionally in combination with one or more of the embodiments described above or below, the composition for use further comprises an antirheumatic drug.

In one embodiment of the second aspect of the invention, optionally in combination with one or more of the embodiments described above or below, the composition is for use in combination therapy for the prevention or treatment of rheumatoid arthritis, wherein the therapy comprises administering to a subject simultaneously, sequentially or separately the composition and an antirheumatic drug. In an even more particular embodiment, the therapy comprises administering to a subject simultaneously, sequentially or separately a dosage unit of the composition comprising from 70 mg to 300 mg of pea protein, from 50 to 200 mg of alpha-glucooligosaccharide, and from 50 to 200 mg of acacia gum; and a dosage unit comprising from 5 to 60 mg of prednisolone, per day.

For the purposes of the present invention, "antirheumatic drug" is a compound or agent that ameliorates or reverses the symptoms and/or progression of autoimmune arthritis, in particular rheumatoid arthritis. Typically, antirheumatic drugs include disease-modifying antirheumatic drugs (DMARDs), non-steroidal anti-inflammatory agents (NSAIDs), analgesics, and corticosteroids. Thus, in a more particular embodiment of the second aspect of the invention, optionally in combination with one or more of the embodiments described above or below, the antirheumatic drug is selected from the group consisting of disease-modifying antirheumatic drug (DMARD), non-steroidal anti-inflammatory agent (NSAID), corticosteroid, analgesic, and combinations thereof.

The term "disease-modifying antirheumatic drug" or "DMARD" refers to a compound or agent capable of slowing down RA progression, and include, for instance, methotrexate, sulfasalazine, hydroxychloroquine, cyclosporine and leflunomide. It belongs to the general common knowledge of the skilled in the art which are the treatments encompassed in this category, as described, for example, in the literature review Benjamin O. et al., "Disease Modifying Anti-Rheumatic Drugs (DMARD)" StatPearls, 2021. This category is also meant to encompass biologic DMARDs, such as monoclonal antibodies that target immune system pathways. In a particular embodiment, the disease-modifying antirheumatic drug is selected from the group consisting of methotrexate, sulfasalazine, hydroxychloroquine, leflunomide, tocilizumab (Actemra), sarilumab (Kevzara), anakinra (Kineret), abatacept (Orencia), rituximab (Rituxan), adalimumab, and azathioprine.

The term "non-steroidal anti-inflammatory agent" or "NSAID" refers to a nonsteroidal anti-inflammatory compound or a nonsteroidal anti-inflammatory drug. NSAIDs inhibit cyclooxygenase, the enzyme responsible for the biosynthesis of the prostaglandins and certain autocoid inhibitors, including inhibitors of the various isozymes of cyclooxygenase (including but not limited to cyclooxygenase-1 and -2), and as inhibitors of both cyclooxygenase and lipoxygenase. Methods of synthesizing NSAIDs are well known in the art and such compounds are also commercially available. Illustrative examples include Advil, Aleve, ibuprofen, naproxen sodium, Tylenol, and Nimesulide. Additional examples include, without limitation, acetic acid derivatives (e.g., acematacin, clindanac, diclofenac, felbinac, fenclofenac, fentiazac, furofenac, indomethacin, isoxepac, ketorolac, oxepinac, sulindac, tiopinac, tolmetin, zidometacin and zomepirac), benorylate, diflunisal, disalcid, fenamates (e.g., flufenamic, meclofenamic, mefenamic, niflumic and tolfenamic acids), fendosal, oxicams (e.g., CP-14,304, isoxicam, piroxicam, sudoxicarn, and tenoxicam), propionic acid derivatives (e.g., alminoprofen, benoxaprofen, carprofen, fenbufen, fenoprofen, flurbiprofen, ibuprofen, indopropfen, ketoprofen, miroprofen, naproxen, oxaprozin, pirprofen, pranoprofen, suprofen, tiaprofenic and tioxaprofen), pyrazoles (e.g., azapropazone, feprazone, oxyphenbutazone, phenylbutazone and trimethazone), safapryn, solprin, trilisate.

As used herein, the term "corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Methods of synthesizing corticosteroids are well known in the art and such compounds are also commercially available. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate.

As used herein, the term "analgesic" refers to a drug that alleviates or prevents pain. For example, the analgesic may be paracetamol.

Thus, in a particular embodiment of the second aspect, optionally in combination with any of the embodiments provided above or below, the corticosteroid is selected from the group consisting of betamethasone, budenoside, cortisone, dexamethasone, hydrocortisone, methylprednisone, prednisolone, prednisone, triamcinolone, and combinations thereof.

In one embodiment of the second aspect of the invention, optionally in combination with one or more of the embodiments described above or below, the composition for use comprises pea protein, acacia gum, alpha-glucooligosaccharide, and a corticosteroid. In an even more particular embodiment, the composition for use comprises pea protein, acacia gum, alpha-glucooligosaccharide, and prednisolone. Even in a more particular embodiment, the composition for use comprises pea protein, acacia gum, alpha-glucooligosaccharide, and prednisolone at a weight ratio from 1.4:0.5:0.5:0.05 to 1.4:2:2:0.2. In a more particular embodiment, the composition for use comprises pea protein, acacia gum, alpha-glucooligosaccharide, and prednisolone at a weight ratio 1.4:1:1:0.1.

In one embodiment of the second aspect of the invention, optionally in combination with one or more of the embodiments described above or below, the composition is administered in the form of a pharmaceutical composition together with one or more pharmaceutically acceptable excipients and/or carriers; or in the form of a nutraceutical product.

The expression "pharmaceutically acceptable excipients and/or carriers" refers to pharmaceutically or veterinary acceptable materials, compositions or vehicles. Each component must be pharmaceutically or veterinary acceptable in the sense of being compatible with the other ingredients of the pharmaceutical or veterinary composition. It must also be suitable for use in contact with the tissue or organ of humans and animals without excessive toxicity, irritation, allergic response, immunogenicity or other problems or complications commensurate with a reasonable benefit/risk ratio.

As used in the present invention, the term "nutraceutical product" refers to any substance that is a food or a part of a food, and provides medical or health benefits, including the prevention and treatment of disease. Such products may range from isolated nutrients, dietary supplements and specific diets to genetically engineered designer foods, herbal products and processed foods, such as cereals, soups and beverages. It is important to note that this definition applies to all categories of food and parts of food. This definition also includes a bio-engineered designer vegetable food, functional food or pharmafood.

The composition provided by the present invention may be administered by different routes of administration. Particular routes include but are not limited to oral, sublingual, nasal, aerosol, inhaled, transdermal, transmucosal, intradermal, subcutaneous, intramuscular, intraperitoneal, intravenous, intrathecal or rectal route. Thus, in one embodiment of the second aspect, the composition is administered in the form of an oral composition.

As above described, in a third aspect the invention provides a composition comprising pea protein, alpha-glucooligosaccharide, acacia gum, and an antirheumatic drug. All the embodiments above provided for the first and second aspects of the invention are also meant to apply to this third aspect.

In one embodiment of the third aspect of the invention, optionally in combination with one or more of the embodiments described above or below, the composition consists on pea protein, alpha-glucooligosaccharide, acacia gum, and antirheumatic drug.

In one embodiment of the third aspect of the invention, optionally in combination with one or more of the embodiments described above or below, the antirheumatic drug is selected from the group consisting of disease-modifying antirheumatic drug (DMARD), non-steroidal anti-inflammatory agent (NSAID), corticosteroid, analgesic, and combinations thereof. In a more particular embodiment, the antirheumatic drug is prednisolone.

In one embodiment of the third aspect of the invention, optionally in combination with one or more of the embodiments described above or below, the composition comprises from 1 w/w to 100% w/w, from 10% w/w to 80% w/w, from 20% w/w to 60% w/w, from 30% w/w to 50% w/w, or from 35% w/w to 45% w/w of pea protein; from 1% w/w to 99% w/w, from 10% w/w to 80% w/w, or from 20% w/w to 40% w/w, of alpha-glucooligosaccharide; from 1% w/w to 99% w/w, from 10% w/w to 80% w/w, or from 20% w/w to 40% w/w, of acacia gum; and from 0.5% w/w to 10% w/w, from 1% w/w to 5% w/w, or from 2% w/w to 4% w/w, of prednisolone, provided that the sum does not exceed 100%. In an even more particular embodiment, the composition comprises 41.18% w/w of pea protein, 29.41% w/w of alpha-glucooligosaccharide; 29.41% w/w of acacia gum, and 2.86% of prednisolone.

In a fourth aspect, the invention provides a pharmaceutical composition comprising a therapeutically effective amount of pea protein, alpha-glucooligosaccharide, acacia gum, and antirheumatic drug, with at least one pharmaceutically acceptable excipient or carrier.

The expression "pharmaceutical composition" encompasses both compositions intended for human as well as compositions for other non-human mammals (i.e., veterinarian compositions).

The expression "therapeutically effective amount" as used herein, refers to the amount of the compound that, when administered, is sufficient to prevent development of, or alleviate to some extent, one or more of the symptoms of the disease which is addressed (i.e. RA). The particular dose of compound administered according to this invention will of course be determined by the particular circumstances surrounding the case, including the compound administered, the route of administration, the particular condition being treated, and the similar considerations.

Examples of suitable pharmaceutically acceptable excipients are solvents, dispersion media, diluents, or other liquid vehicles, dispersion or suspension aids, surface active agents, isotonic agents, thickening or emulsifying agents, preservatives, solid binders, lubricants and the like. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Excipients such as colouring agents, coating agents, sweetening, and flavouring agents can be present in the composition, according to the judgment of the formulator.

The pharmaceutical compositions containing the compound of the invention can be presented in any dosage form, for example, solid or liquid, and can be administered by any suitable route, for example, oral, parenteral, rectal, topical, intranasal or sublingual route, for which they will include the pharmaceutically acceptable excipients necessary for the formulation of the desired dosage form, for example, topical formulations (ointment, creams, lipogel, hydrogel, etc.), eye drops, aerosol sprays, injectable solutions, osmotic pumps, etc.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, corn-starch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary binding agents include, but are not limited to, starch (e.g., corn-starch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminium silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, ascorbyl palmitate, ascorbyl stearate, ascorbyl oleate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

In a fifth aspect, the invention provides the composition as defined in the third aspect or the pharmaceutical composition as defined in the fourth aspect for use as a medicament.

The pea protein for use as defined in the first aspect, composition for use as defined in the second aspect, the composition as defined in the third aspect, or the pharmaceutical composition as defined in the fourth aspect, can be prepared by conventional methods known to those skilled in the art.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

Materials and Methods

Pea protein was purchased from Cosucra (Pisane® F9), Acacia senegal powder was purchased from Nexira (Fibregum P), alpha-glucooligosaccharide was purchased from Solabia Group (BioEcolians®), and prednisolone was purchased from Sigma Aldrich (prednisolone 21-sodium succinate, P-4153).

Each compound (140 mg of pea protein; 100 mg of Acacia gum; and 100 mg of alpha-Glucooligosaccharide) were administered in a PBS solution via oral gavage daily, from day 0 to day 14 in mice of Group A, and from day 4 to day 14 in mice of Group B. Prednisolone was administered via oral gavage at the doses of 0.05, 0.2 and 1 mg/kg as disclosed in Oosten, L., Helsen, M., Saxne, T. et al. "Synergistic protection against cartilage destruction by low dose prednisolone and interleukin-10 in established murine collagen arthritis". Inflamm. Res. 48, 48-55, 1999.

Specific pathogen-free Male BALB/c mice (Envigo, Milan, Italy) were used for experiment. The cages and the housing room were periodically cleaned. The animals were fed with standard pellet complete diet supplied by the authorized breeder. Filtered tap water from local network were supplied ad libitum. The animals were kept in quarantine area for one week before used in the study. During this period they were daily observed. At the end of the quarantine week, the animals were carefully examined in order to evaluate their suitability for the study.

Male BALB/c mice (4 to 6-week-old) were housed in a controlled environment (22±2° C., 55±15% relative humidity, 12 h light/dark cycle). After a one-week acclimation, mice were fed with a standard diet and water.

Collagen antibody-induced arthritis (CAIA) was induced in the mice as disclosed in Terato, K., et al., "Induction of arthritis with monoclonal antibodies to collagen" J. Immunol., 1992, vol. 148(7), pp. 2103-8, using an arthritogenic monoclonal antibodies (mAb) cocktail. The mAb cocktail contained three mAb (F10, A2, D8) of type IgG2a and one mAb (D1) of type IgG2b in equal amounts, directed to bovine CII (Arthrogen-CIA, Chondrex) suspended in sterile PBS. All WT mice received intraperitnoeal i.p. injections of 8 mg/mouse of Arthrogen on day 0 and 50 μg/mouse of LPS from E. coli strain 0111B4 (Sigma, T 3382) on day 3 to synchronize the development of arthritis. All mice started to develop arthritis at day 4 and were sacrificed at day 14.

The animals were divided into the following two groups:
Group A: the animals were administered with the therapeutic compounds from day 0 to day 14.
Group B: the animals were administered with the therapeutic compounds from day 4 to day 14.

Animals from group A and B were separated in some the following subgroups, depending on the assay, and administered with the indicated compounds or combination of compounds:

1. Sham+vehicle (negative control) (n=3)
2. Sham+prednisolone 0.05 mg/kg (n=3)
3. Sham+prednisolone 0.05 mg/kg+MD (50 mg acacia gum (AG)+70 mg pea protein (PP)+50 mg alpha-GOS) (n=3)
4. Sham+prednisolone 0.2 mg/kg (n=3)
5. Sham+prednisolone 0.2 mg/kg+MD (50 mg AG+70 mg PP+50 mg alpha-GOS) (n=3)
6. Sham+prednisolone 1 mg/kg (n=3)
7. Sham+prednisolone 1 mg/kg+MD (50 mg AG+70 mg PP+50 mg alpha-GOS) (n=3)
8. Sham+MD (n=3)
9. CAIA+vehicle (positive control) (n=6)
10. CAIA+prednisolone 0.05 mg/kg (n=6)
11. CAIA+prednisolone 0.05 mg/kg+MD (50 mg AG+70 mg PP+50 mg alpha-GOS) (n=6)
12. CAIA+prednisolone 0.2 mg/kg (n=6)
13. CAIA+prednisolone 0.2 mg/kg (n=6)+MD (50 mg AG+70 mg PP+50 mg alpha-GOS) (n=6)
14. CAIA+prednisolone 1 mg/kg (n=6)
15. CAIA+prednisolone 1 mg/kg+MD (50 mg AG+70 mg PP+50 mg alpha-GOS) (n=6)
16. CAIA+MD (100 mg AG+140 mg PP+100 mg alpha-GOS) (n=6)
17. CAIA+140 mg Pea Protein (n=6)
18. CAIA+MD (150 mg AG+200 mg PP+150 mg alpha-GOS) (n=6)
19. CAIA+200 mg Pea Protein (n=6)
20. CAIA+MD (50 mg AG+70 mg PP+50 mg alpha-GOS) (n=6)
21. CAIA+70 mg Pea Protein (n=6)

Sham represents mice not subjected to collagen antibody-induced arthritis induction.

Radiological analysis was carried out using X-ray technique, and radio-logical scoring (level: 0=Normal; 1=Slight; 2=Moderate and 3=Severe) was calculated considering different parameters such as periosteal reaction/hypertrophy, bone erosion, soft tissue swelling, narrowed joint space and osteoporosis in the ankle-joints, as described in Balkrishna A, et al., "Herbo-mineral formulation 'Ashwashila' attenuates rheumatoid arthritis symptoms in collagen-antibody-induced arthritis (CAIA) mice model" Sci Rep., 2019; vol. 9(1); pp. 8025.

Histological analysis was carried out as previously described (Balkrishna A, et al., supra; Mengdi et al., "A novel dexamethasone-loaded liposome alleviates rheumatoid arthritis in rats"; International Journal of Pharmaceutics; 2018; vol. 540 (1-2); pp. 57-64) and indicating score analysis of the RA disease-associated lesions such as the moderately enlarged synovial membrane, hyperplastic synovium, the presence of inflammation and bone and cartilage erosion on a 0-4 scale as follows: 0=normal; 1=mild, slight swelling; 2=moderate swelling; 3=severe swelling; 4=maximally inflamed; 5=extremally inflamed.

Real-time PCR assays were carried out as previously described (Marjan Rashidan et al., "Detection of *B. fragilis* group and diversity of bft enterotoxin and antibiotic resistance markers cepA, cfiA and nim among intestinal *Bacteroides fragilis* strains in patients with inflammatory bowel disease"; Anaerobe; 2018; vol. 50:93; pp. 100), uwsing the following primers:

```
Bacteroides fragilis F:
                                    (SEQ ID NO: 1)
TGATTCCGCATGGTTTCATT Bacteroides fragilis R:
                                    (SEQ ID NO: 2)
CGACCCATAGAGCCTTCATC Collinsella sp F:
                                    (SEQ ID NO: 3)
CCCGACGGGAGGGGAT Collinsella sp R:
                                    (SEQ ID NO: 4)
CTTCTGCAGGTACAGTCTTGAC Prevotella F:
                                    (SEQ ID NO: 5)
CAGCAGCCGCGGTAATA Prevotella R:
                                    (SEQ ID NO: 6)
GGCATCCATCGTTTACCGT
```

Results

1. Radiographic Analysis

In RA, the activation of the immune system leads to progressive destruction of synovial joints. Bone degradation resulting in joint damage was seen in mice treated with vehicle (Group 9), compared to control groups (Groups 1-8), as showed in Tables 1 and 2:

Treatment with pea protein at various doses, alone (Groups 17, 19, 21) or in combination with acacia gum and alfa-GOS (Groups 16, 18, 20), significantly suppressed the extent of new bone resorption, reducing bone erosion and cartilage destruction in the joints, to an extent comparable with prednisolone treated mice at low or medium doses (Groups 10 and 12).

These results show that pea protein alone or in combination with acacia gum and alfa-GOS are efficient in preventing and reducing RA progression.

Importantly, administering pea protein, acacia gum and alfa-GOS together with prednisolone synergistically increased prednisolone action (Groups 11, 13, and 15). These results show that the combination of pea protein, acacia gum and alfa-GOS allows to reduce corticosteroid concentration while maintaining its therapeutic efficacy for treating RA, thereby reducing its potential side-effects.

2. Histological Analysis

Histopathological analysis of the CAIA mice hind legs was performed following fourteen days of treatment. Ankle-joints analysis of the CAIA mice was performed indicating the development of arthritis disease-associated lesions such as the moderately enlarged synovial membrane, hyperplastic synovium, increased synovial vascularity, the presence of inflammation and, bone and cartilage erosion.

Not detectable histological damage was reported in Sham mice belonging to the Groups 1-8; while, the onset of arthritis in the CAIA animals (Group 9) following C-Ab and LPS treatments was visible through an increase in histological score compared to the Sham mice (p-value≤0.01).

As shown in Tables 3 and 4, significant reduction in the ankle-joint lesion scores was observed in the CAIA mice following treatments with pea protein at various doses, alone or in combination with acacia gum and alfa-GOS (Groups 16-21).

TABLE 1

Radiological score in mice of group A in the subgroups indicated.

| | 1A-8A | 9A | 10A | 11A | 12A | 13A | 14A | 15A | 16A | 17A | 18A | 19A | 20A | 21A |
|---|---|---|---|---|---|---|---|---|---|---|---|---|---|---|
| MEAN | 0.0 | 2.5 | 2.3 | 2.3 | 1.8 | 1.3 | 1.7 | 1.7 | 1.8 | 1.8 | 1.6 | 1.8 | 1.8 | 1.8 |
| SEM | 0.0 | 0.2 | 0.1 | 0.1 | 0.1 | 0.1 | 0.1 | 0.1 | 0.1 | 0.1 | 0.2 | 0.1 | 0.2 | 0.1 |
| | | *** | | | ## | ### | ### | ### | # | # | ### | ## | ## | ## |

***P < 0.001 vs sham (1A); ### P < 0.001, ##P < 0.01 and #p < 0.05 vs CAIA (9A).

TABLE 2

Radiological score in mice of group B in the subgroups indicated.

| | 1B-8B | 9B | 10B | 11B | 12B | 13B | 14B | 15B | 16B | 17B | 18B | 19B | 20B | 21B |
|---|---|---|---|---|---|---|---|---|---|---|---|---|---|---|
| MEAN | 0.0 | 2.7 | 2.6 | 2.5 | 1.9 | 1.6 | 1.8 | 1.3 | 1.9 | 1.9 | 1.9 | 1.9 | 2.0 | 1.9 |
| SEM | 0.0 | 0.1 | 0.1 | 0.1 | 0.1 | 0.1 | 0.1 | 0.1 | 0.1 | 0.2 | 0.2 | 0.2 | 0.1 | 0.2 |
| | | *** | | | ## | ### | ### | ### | ## | ## | ## | ## | # | ## |

***P < 0.001 vs sham (1B); ### P < 0.001, ##P < 0.01 and #p < 0.05 vs CAIA (9B).

TABLE 3

Histological score in mice of group A in the subgroups indicated.

| | 1A-8A | 9A | 10A | 11A | 12A | 13A | 14A | 15A | 16A | 17A | 18A | 19A | 20A | 21A |
|---|---|---|---|---|---|---|---|---|---|---|---|---|---|---|
| MEAN | 0.0 | 2.2 | 1.8 | 1.6 | 1.3 | 0.6 | 1.1 | 1.5 | 1.1 | 1.1 | 0.6 | 0.6 | 1.5 | 0.6 |
| SEM | 0.0 | 0.4 | 0.2 | 0.1 | 0.1 | 0.1 | 0.1 | 0.1 | 0.0 | 0.1 | 0.1 | 0.1 | 0.1 | 0.1 |
| | | ** | | # | ### | ### | ### | ## | ### | ### | ### | ### | ## | ### |

**$P < 0.01$ vs sham (1A); ### $P < 0.001$, ##$P < 0.01$ and #$p < 0.05$ vs CAIA (9B)

TABLE 4

Histological score in mice of group B in the subgroups indicated.

| | 1B-8B | 9B | 10B | 11B | 12B | 13B | 14B | 15B | 16B | 17B | 18B | 19B | 20B | 21B |
|---|---|---|---|---|---|---|---|---|---|---|---|---|---|---|
| MEAN | 0.0 | 2.5 | 2.4 | 2.1 | 1.8 | 1.1 | 1.9 | 1.5 | 1.5 | 0.6 | 1.1 | 1.8 | 1.2 | 0.7 |
| SEM | 0.0 | 0.2 | 0.1 | 0.1 | 0.1 | 0.0 | 0.1 | 0.1 | 0.2 | 0.1 | 0.1 | 0.1 | 0.2 | 0.1 |
| | | ** | | | ### | ### | # | ### | ### | ### | ### | | ### | ### |

**$P < 0.01$ vs sham (1B); ### $P < 0.001$, ##$P < 0.01$ and #$p < 0.05$ vs CAIA (9B).

Notably, mice treated with the three components together with prednisolone exhibited synergistically improved lesion-reducing efficacy in the synovial membrane inflammation, cartilage, and bone erosions (Groups 11, 13 and 15).

3. Measurement of Cytokine in Arthritic Hind Paws

After sacrifice, mice hind paws were surgically removed and processed for ELISA kit (Mouse IL17A ELISA Kit-LS-F24837, LSBio; Mouse IL-6 ELISA Kit-ab100713, Abcam; Mouse IL-23 ELISA Kit-MBS494788, MyBiosource; Mouse IL-1 beta ELISA Kit-ab100705, Abcam; Mouse TNF alpha ELISA Kit-MBS825075; MyBiosource) according to manufacturer's instructions, in order to evaluate cytokines levels after CAIA induction. Cytokines regulate a wide range of inflammatory processes involved in the pathogenesis of rheumatoid arthritis; in fact, it is well known that an imbalance between the activities of pro- and anti-inflammatory cytokines favors the induction of autoimmunity, chronic inflammation and consequently tissue damage.

Figure 2:
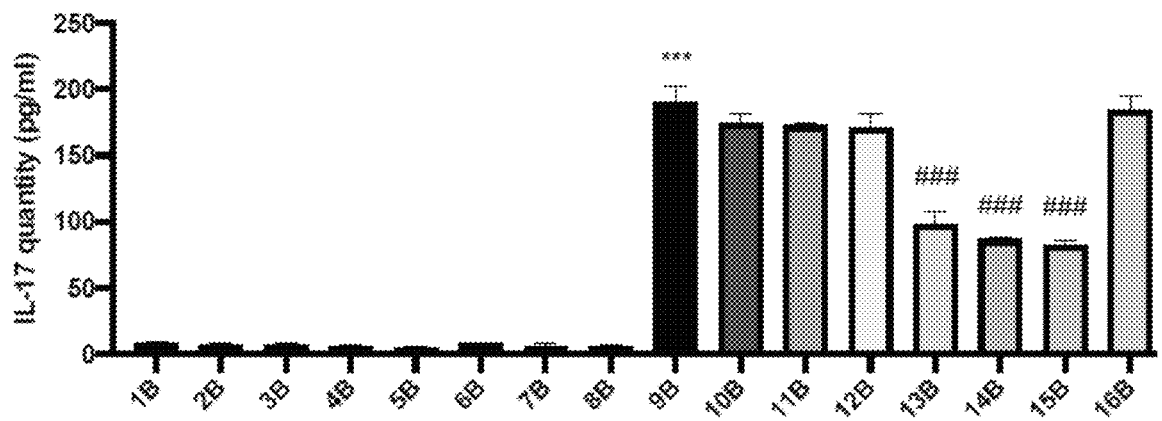
FIG. 2 shows the evaluation of cytokine in arthritic hind paws of mice from group B. Values are indicated as the mean±SEM. ***P<0.001 vs sham (1B); ###P<0.001, ##P<0.01 and #p<0.005 vs CAIA (9B).
Figure 2:
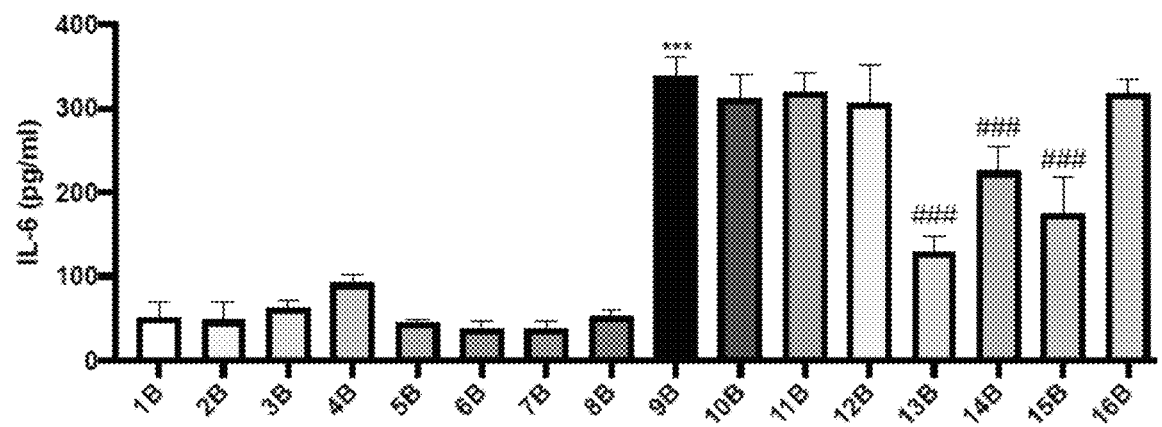
Figure 2:
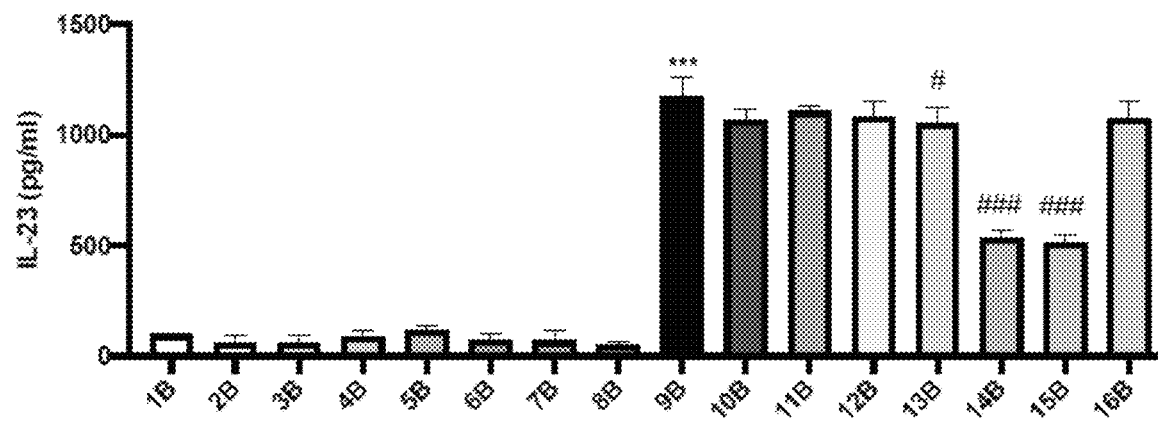
Figure 2:
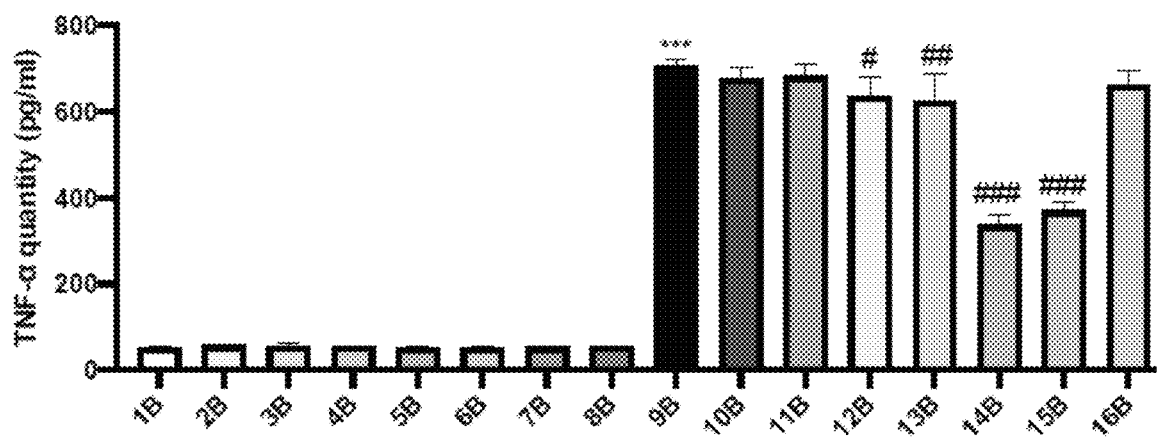
Figure 2:
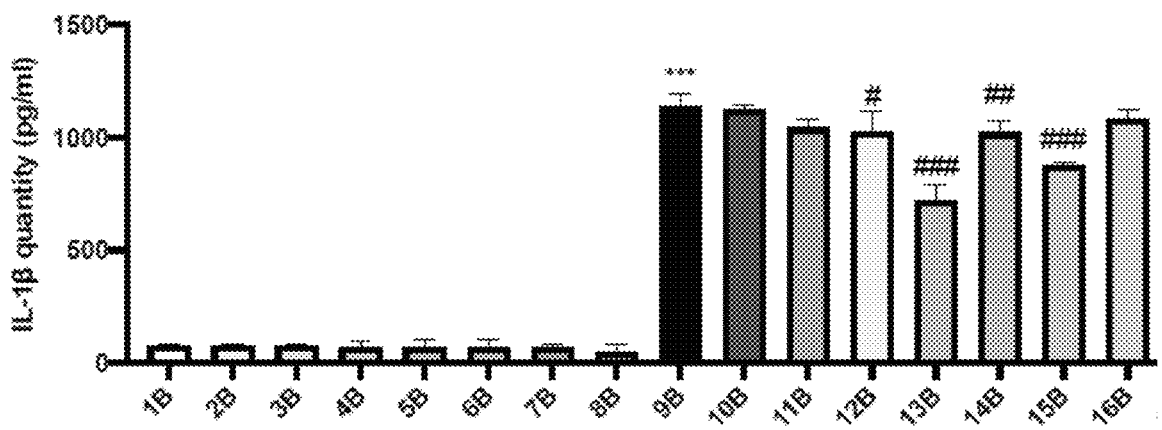

A noticeable increase in cytokine levels (IL-17, IL-6, IL-23, TNF-α and IL-1β) was detected in CAIA mice (group 9), compared to the sham group (groups 1-8) (FIGS. 1-2).

Treatment with prednisolone at high doses significantly reduced the expressions of the aforementioned cytokines (group 14). Importantly, this reduction was highly potentiated when prednisolone treatment was combined with pea protein, acacia gum, and alpha-GOS administration (groups 13 and 15). In particular, pea protein, acacia gum, and alpha-GOS allowed reducing cytokine levels with much lower doses of prednisolone (group 13).

4. Measurement of Cytokine in Joints

Figure 3:
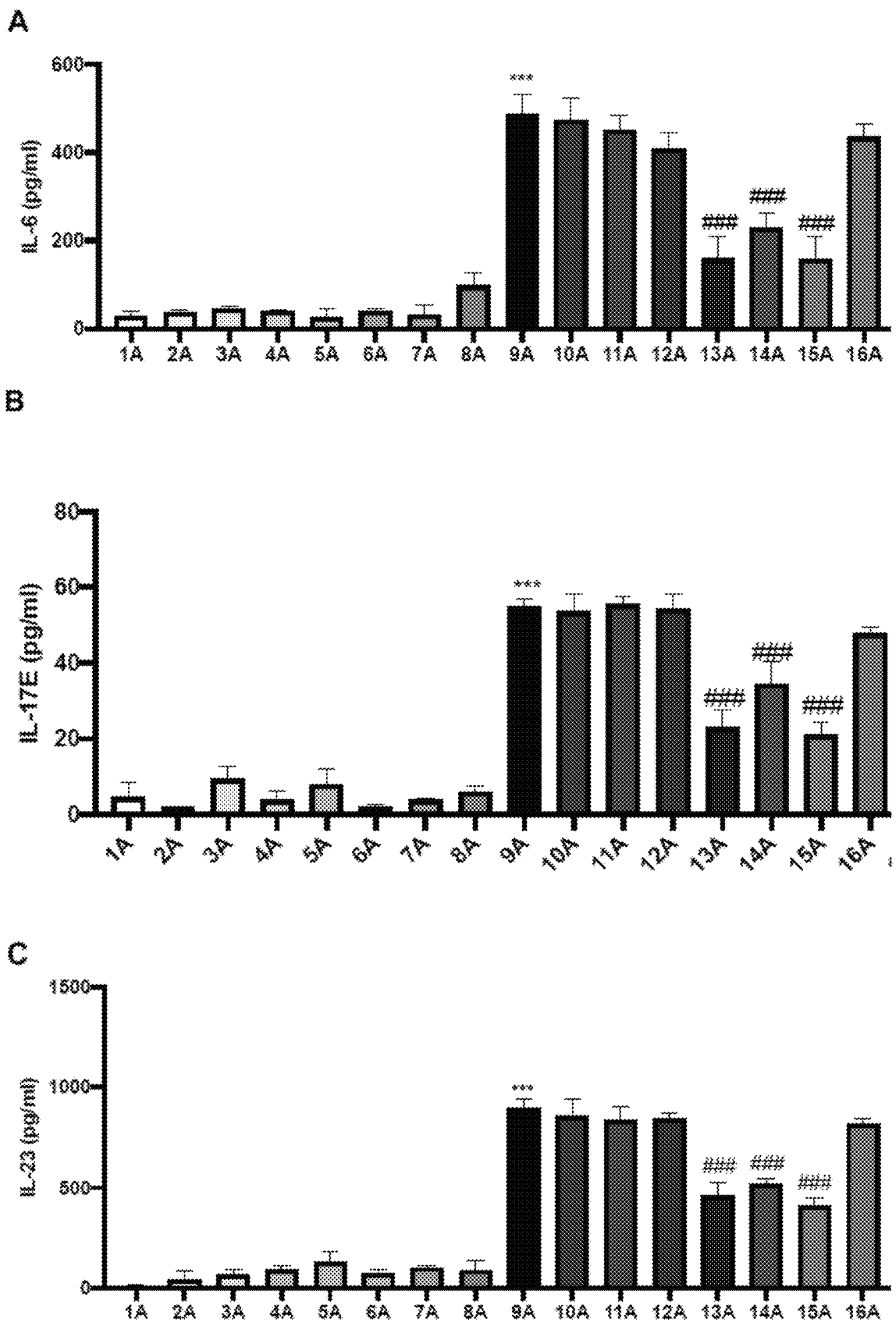
FIG. 3 shows the evaluation of cytokine in joints of mice from group A. Values are indicated as the mean±SEM. *** p<0.001 vs Sham (1A); ###p<0.001 vs CAIA (9A).
Figure 4:
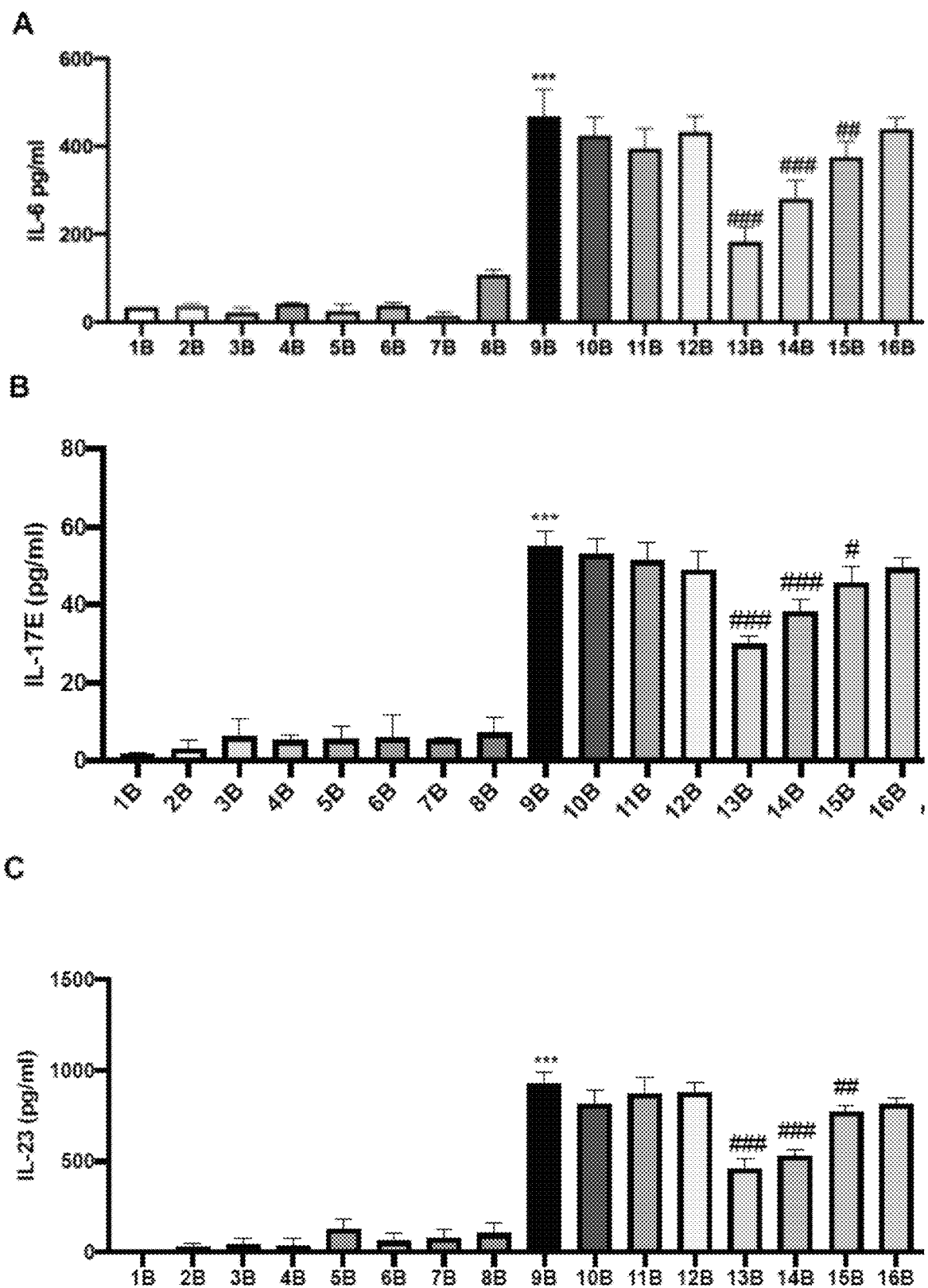
FIG. 4 shows the evaluation of cytokine in joints of mice from group B. Values are indicated as the mean±SEM. *** p<0.001 vs Sham (1B); #p<0.05, ##p<0.01, ###p<0.001 vs CAIA (9B).

Joint samples were processed for ELISA assay to detect the levels of pro-inflammatory cytokines IL-6, IL-17 and IL-23. The results obtained from joint lysates showed that mice treated with pea protein, acacia gum, and alpha-GOS in combination with prednisolone (FIGS. 3-4) (Groups 11, 13, 15) had lowered cytokine levels compared to mice only treated with prednisolone or with the other three compounds (Groups 10, 12, 14, 16).

Also noticeable, mice treated only with pea protein, acacia gum, and alpha-GOS (i.e. without prednisolone) showed a decrease in IL-6, IL-17 and IL-23 levels compared to the group CAIA (Group 16) which was not shown in mice treated with the single components.

5. Measurement of Cytokine in Blood

Figure 5:
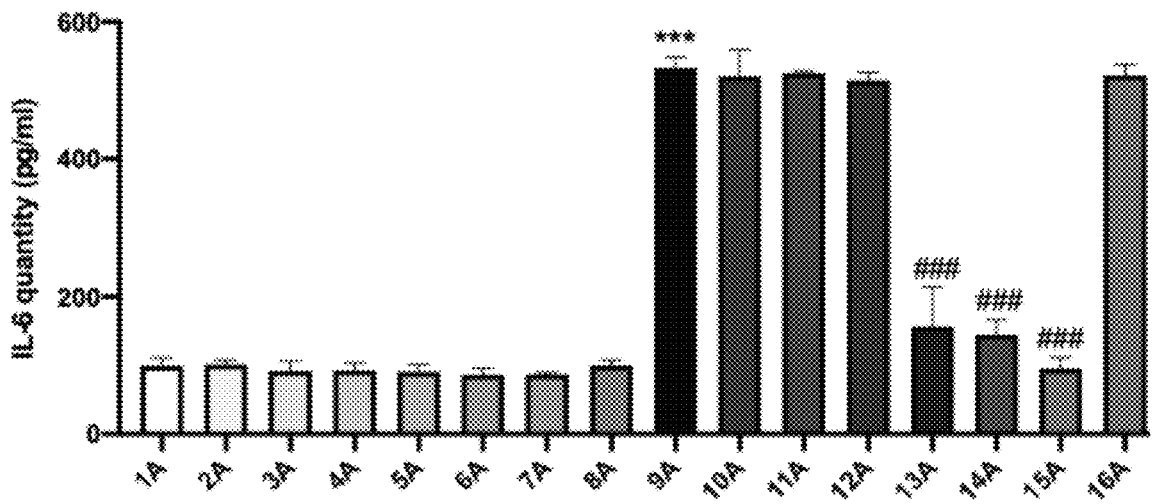
FIG. 5 shows the evaluation of cytokines in blood from mice of group A. Values are indicated as the mean±SEM. *** p<0.001 vs Sham (1A). #p<0.05, ###p<0.001 vs CAIA (9A).
Figure 5:
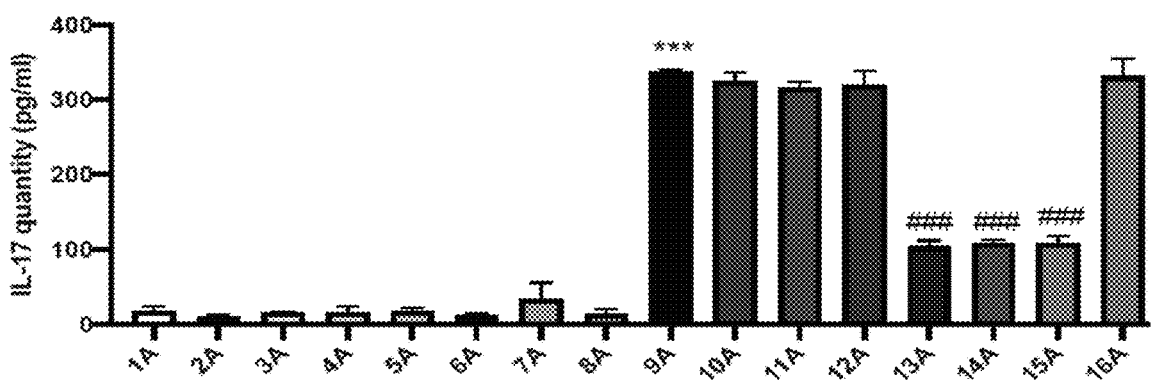
Figure 5:
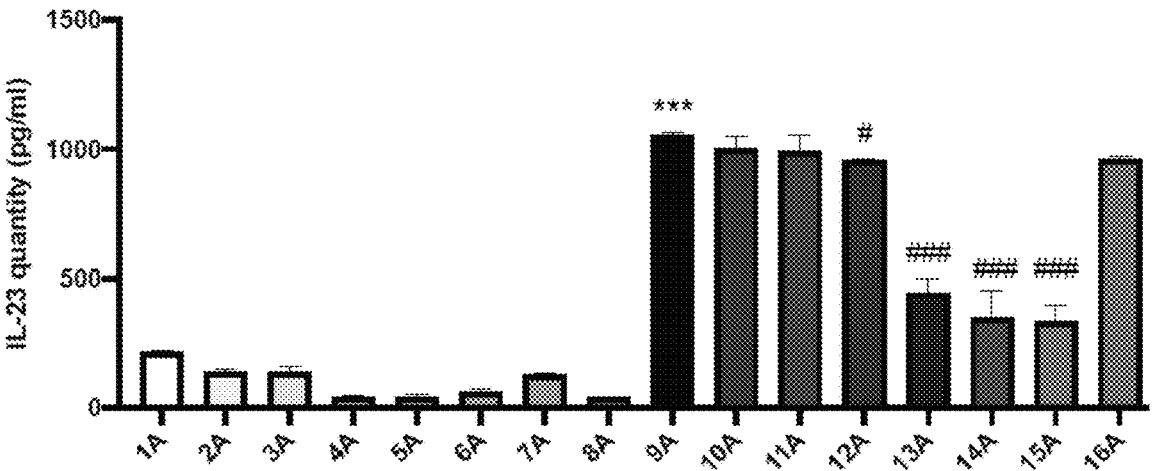
Figure 6:
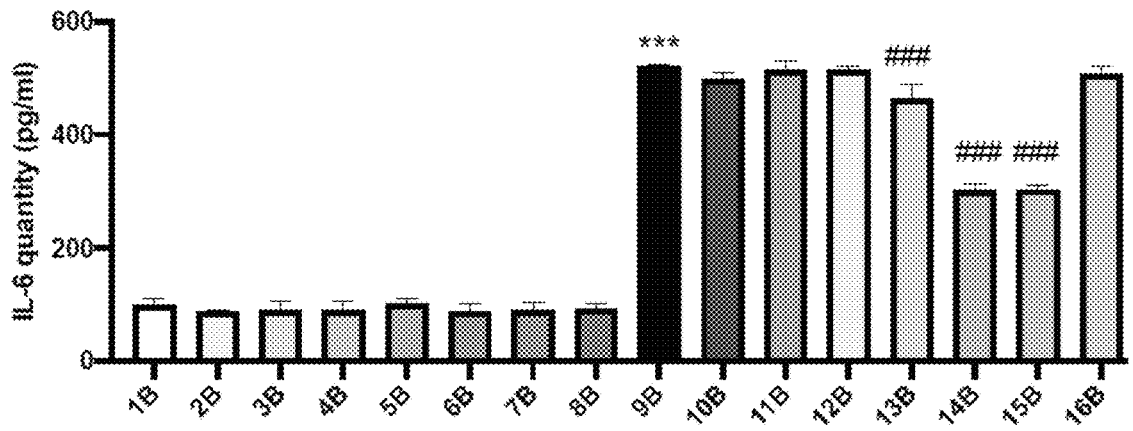
FIG. 6 shows the evaluation of cytokines in blood from mice of group B. Values are indicated as the mean±SEM. *** p<0.001 vs Sham (1B). ###p<0.001 vs CAIA group (9B).
Figure 6:
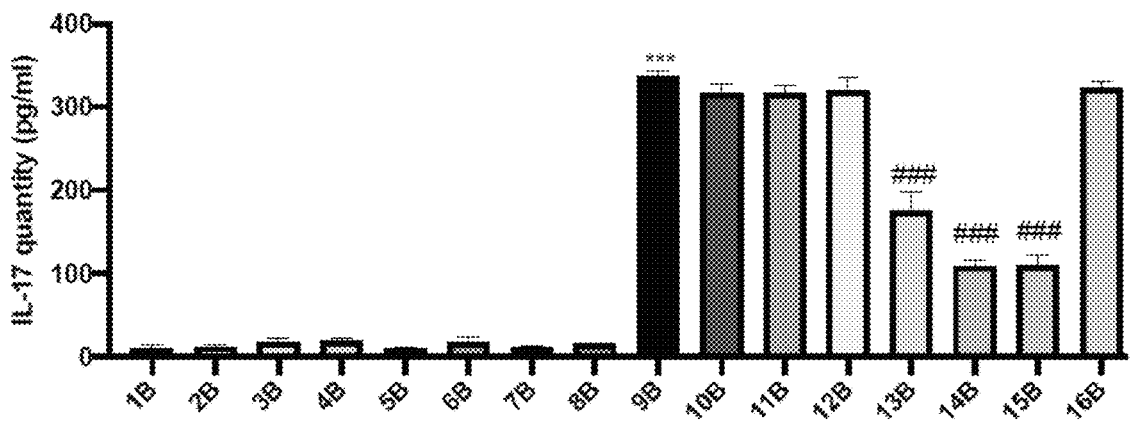
Figure 6:
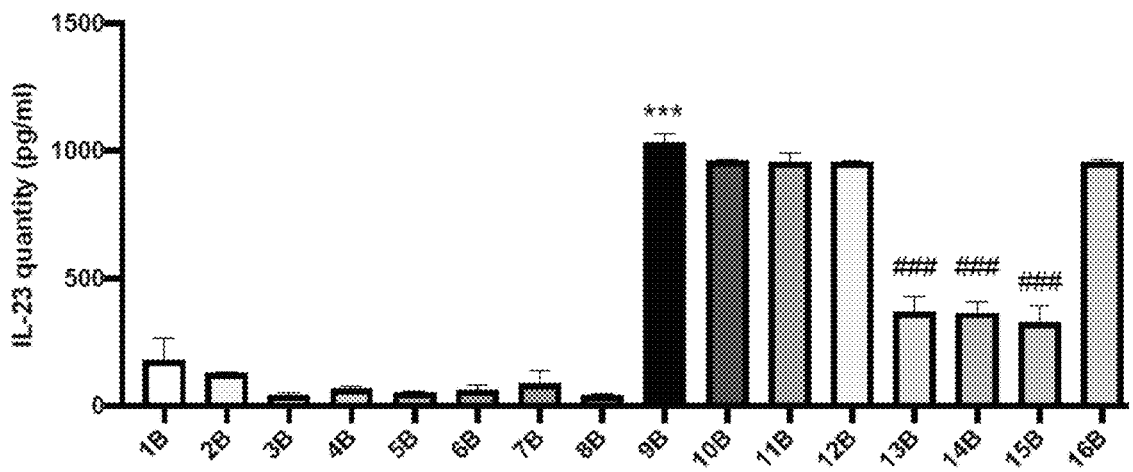
Figure 7:
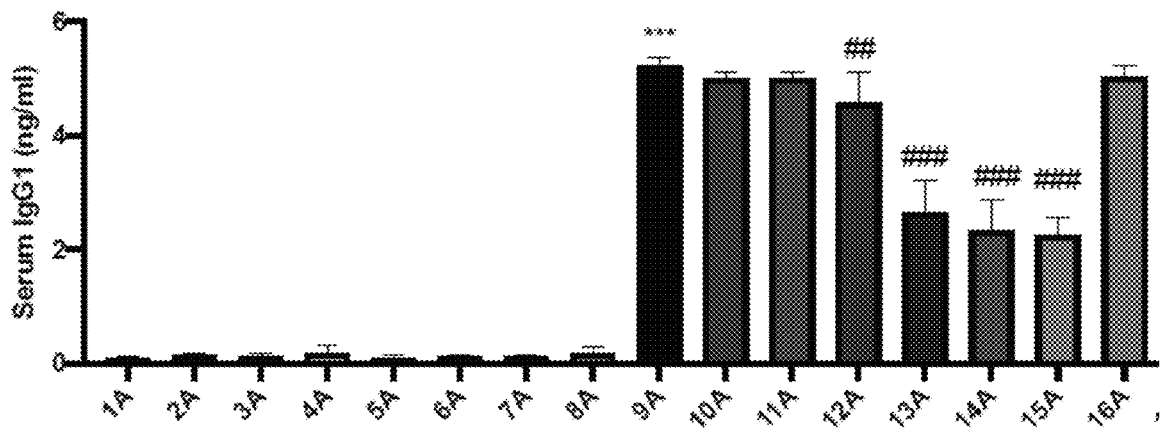
FIG. 7 shows the evaluation of immunoglobulin isotypes from mice of group A. Values are indicated as the mean±SEM. ***P<0.001 vs sham; ###P<0.001, ##P<0.01 and #p<0.005 vs CAIA+MD.
Figure 7:
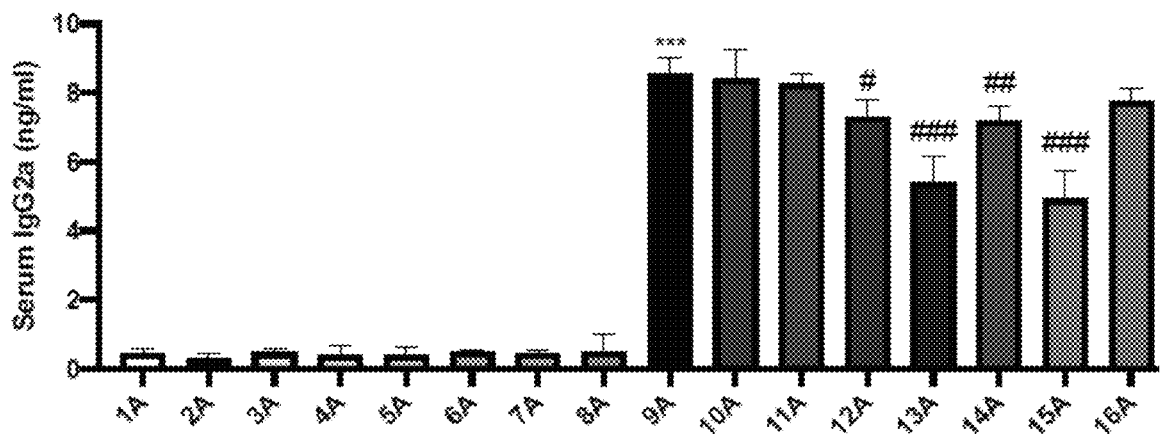
Figure 8:
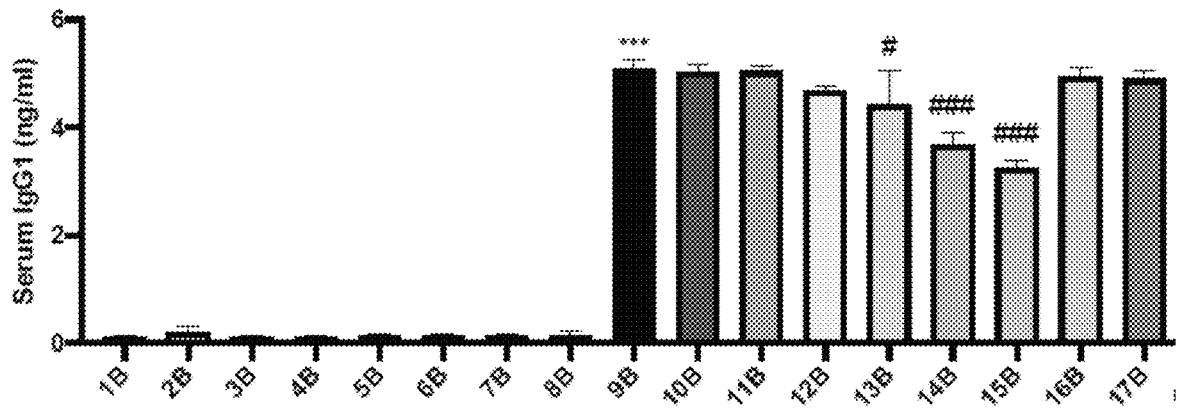
FIG. 8 shows the evaluation of immunoglobulin isotypes from mice of group B. Values are indicated as the mean±SEM. ***P<0.001 vs sham (1B); ###P<0.001 and ##P<0.01 vs CAIA (9B).
Figure 8:
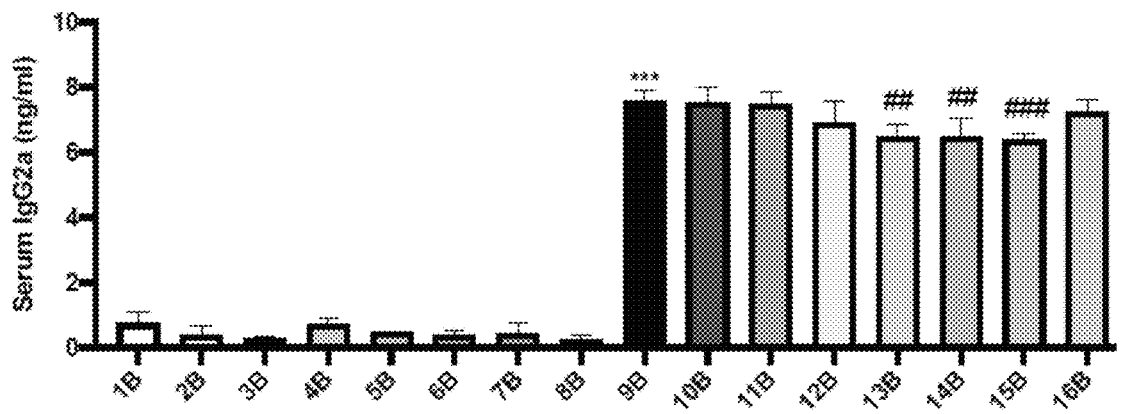

Plasma obtained from the anesthetized mice was used to evaluate the pro-inflammatory cytokines IL-6, IL-17 and IL-23 levels as described above, which also showed a synergistic decrease in cytokine levels in mice treated with the combination of pea protein, acacia gum, and alpha-GOS together with prednisolone (FIG. 5-6, Groups 13 and 15).

6. Measurement of Immunoglobulin Isotypes (Rheumatoid Factors)—Serum Level IgG1 and IgG2a At the end of the experiment, the animals of all groups were sacrificed and the blood collected for biochemical analysis. After obtaining the serum from the blood of each mouse, anti-collagen-II antibodies IgG1 and IgG2a (FIG. 7-8) analyzes were carried out by ELISA kit (Mouse IgG1 ELISA Kit-ab133045, Abcam; Mouse IgG2a ELISA Kit-ab133046, Abcam) following the manufacturer's instructions. A notable increase of IgG1 and IgG2a serum levels was found in CAIA mice compared to the sham groups (Groups 1-8 vs 9).

Like in the previous experiments, administering pea protein, acacia gum, and alpha-GOS in combination with prednisolone synergistically potentiated the effect of the corticosteroid (Groups 10-16), which allowed to further reduce immunoglobulin levels, even at lower prednisolone doses.

7. Evaluation of Bacterial Strains by Real-Time PCR Assays

Microbial composition in new-onset untreated RA patients is shaped if compared with healthy subjects. On this basis, the inventors performed Real-time PCR (R/T-PCR) investigation from fecal samples for bacterial studies in treated mice.

Figure 9:
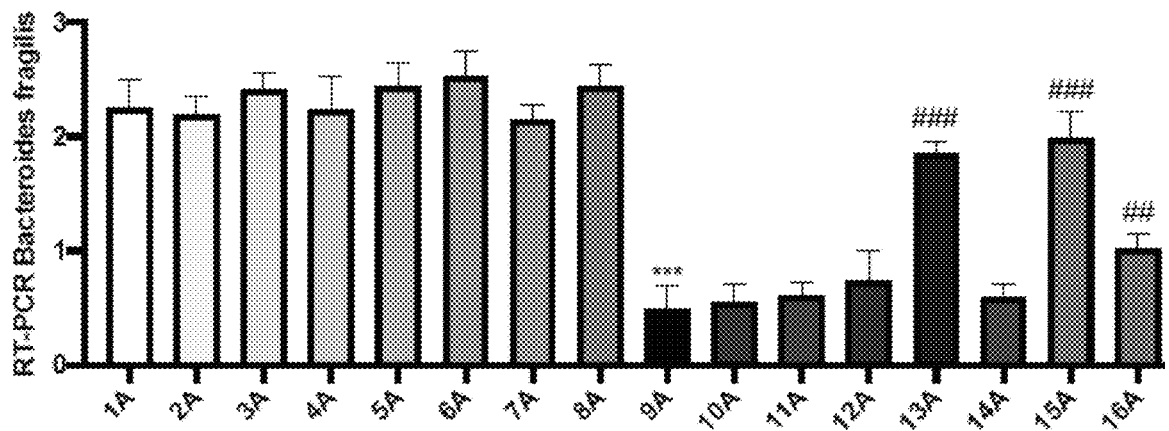
FIG. 9 shows the evaluation of *Bacteroides fragilis* in fecal samples from mice of group A. Values are indicated as the mean±SEM. ***P<0.001 vs sham (1A and B); ###P<0.001, ##P<0.01 and #P<0.05 vs CAIA (9A and B).

A significant decrease in *Bacteroides fragilis* expression was detected in CAIA mice, compared to the sham groups (FIG. 9, Group 9).

Treatment with a combination of pea protein, acacia gum and alpha-GOS considerably restored *Bacteroides fragilis* level (Group 16). The levels were further increased when prednisolone was also administered (Groups 13 and 15), adding further evidence to the synergistic functional effect among these components.

Figure 10:
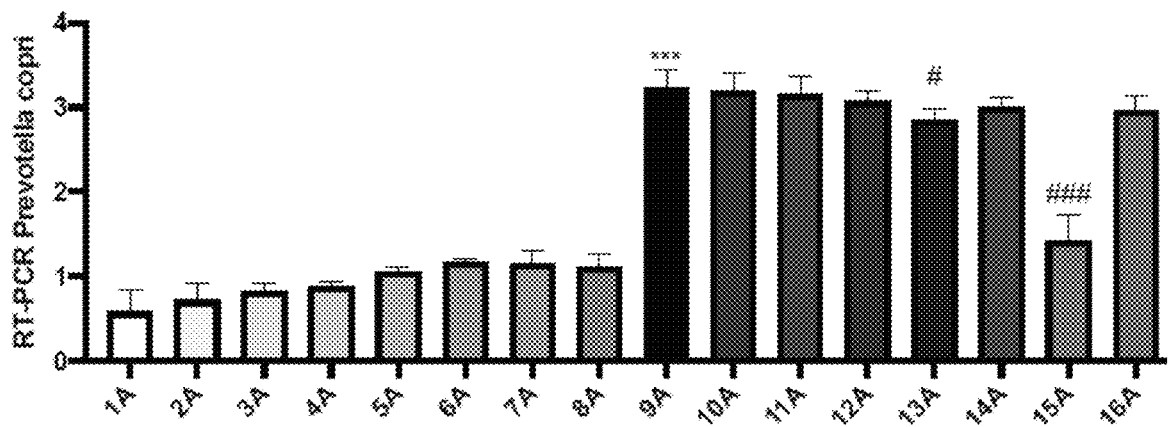
FIG. 10 shows the evaluation of *Prevotella* in fecal samples from mice of group A. Values are indicated as the mean±SEM. ***P<0.001 vs sham (1A and B); ###P<0.001, ##P<0.01 and #P<0.05 vs CAIA (9A and B).

On the other hand, *Prevotella copri* quantification resulted in a considerable increase in CAIA mice, compared to the sham groups (FIG. 10, Group 9). Treatment with pea protein, acacia gum and alpha-GOS at high doses, alone or in combination with prednisolone appreciably reduced *Prevotella copri* fecal levels (Groups 13, 15).

Figure 11:
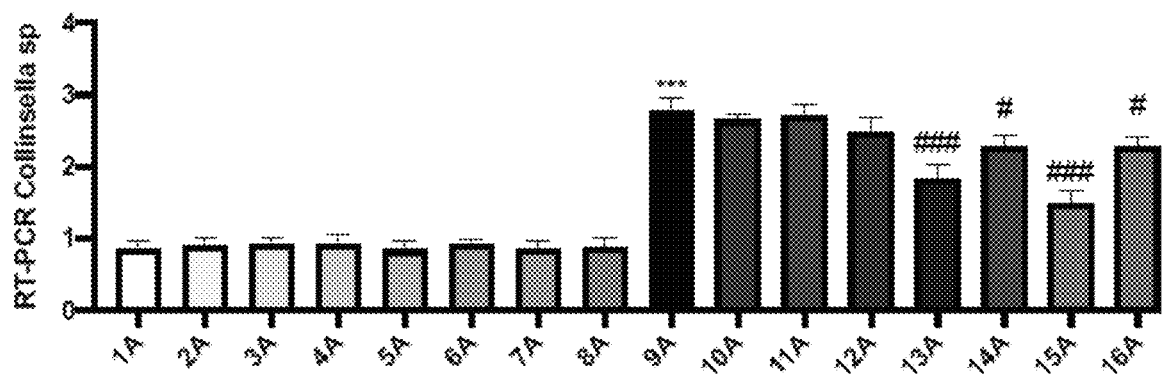
FIG. 11. Evaluation of *Collinsella* in fecal samples from mice of group A. Values are indicated as the mean±SEM. ***P<0.001 vs sham (1A and B); ###P<0.001, ##P<0.01 and #P<0.05 vs CAIA (9A and B).

Assay for *Collinsella* sp showed a significant overexpression in CAIA control mice, compared to the sham groups (FIG. 11, Group 9), which was significantly reduced in mice treated with pea protein, acacia gum and alpha-GOS at high doses, alone or in combination with prednisolone (Groups 13-16).

In conclusion, all these results show that the composition of the invention comprising pea protein is useful for the treatment of autoimmune arthritis, in particular RA. Importantly, they also show that it is particularly useful when combined with acacia gum, alpha-GOS, and an antirheumatic drug, in particular prednisolone.

Citation List

Benjamin O. et al., "Disease Modifying Anti-Rheumatic Drugs (DMARD)" StatPearls, 2021.

Terato, K., et al., "Induction of arthritis with monoclonal antibodies to collagen" J. Immunol., 1992, vol. 148(7), pp. 2103-8.

Oosten, L., Helsen, M., Saxne, T. et al. "Synergistic protection against cartilage destruction by low dose prednisolone and interleukin-10 in established murine collagen arthritis". Inflamm. res. 48, 48-55, 1999.

Balkrishna A, et al., "Herbo-mineral formulation 'Ashwashila' attenuates rheumatoid arthritis symptoms in collagen-antibody-induced arthritis (CAIA) mice model" Sci Rep., 2019; vol. 9(1); pp. 8025.

Mengdi et al., "A novel dexamethasone-loaded liposome alleviates rheumatoid arthritis in rats"; International Journal of Pharmaceutics; 2018; vol. 540 (1-2); pp. 57-64.

Marjan Rashidan et al., "Detection of *B. fragilis* group and diversity of bft enterotoxin and antibiotic resistance markers cepA, cfiA and nim among intestinal *Bacteroides fragilis* strains in patients with inflammatory bowel disease"; Anaerobe; 2018; vol. 50:93; pp. 100

The invention claimed is:

1. A method for treating autoimmune arthritis or preventing autoimmune arthritis progression, the method comprising administering a therapeutically effective amount of a composition comprising pea protein isolate obtained from yellow pea *Pisum sativum* seeds, alpha-glucooligosaccharide, and acacia gum, wherein the weight ratio of pea protein to alpha-glucooligosaccharide to acacia gum (PP:GOS:AG) is from 1.4:0.1:0.1 to 1.4:10:10, to a subject in need thereof.

2. The method according to claim 1, wherein the autoimmune arthritis is selected from the group consisting of rheumatoid arthritis, psoriatic arthritis, ankylosing spondylitis, and juvenile idiopathic arthritis.

3. The method according to claim 2, wherein the autoimmune arthritis is rheumatoid arthritis.

4. The method according to claim 1, wherein the composition comprises pea protein, alpha-glucooligosaccharide, and acacia gum at a weight ratio (PP:GOS:AG) from 1.4:0.5:0.5 to 1.4:5:5.

5. The method according to claim 4, wherein the weight ratio (PP:GOS:AG) is from 1.4:0.5:0.5 to 1.4:2:2.

6. The method according to claim 1, wherein the composition comprises from 10% w/w to 80% w/w of pea protein.

7. The method according to claim 6, wherein the composition comprises from 30% w/w to 50% w/w of pea protein.

8. The method according to claim 1, wherein the prevention or treatment comprises administering to the subject a dosage unit of the composition comprising from 70 mg to 300 mg of pea protein, from 50 to 200 mg of alpha-glucooligosaccharide, and from 50 to 200 mg of acacia gum per day.

9. The method according to claim 1, wherein the composition further comprises an antirheumatic drug.

10. The method according to claim 9, wherein the antirheumatic drug is selected from the group consisting of disease-modifying antirheumatic drug (DMARD), non-steroidal anti-inflammatory agent (NSAID), corticosteroid, analgesic, and combinations thereof.

11. The method according to claim 10, wherein the corticosteroid is prednisolone.

12. The method according to claim 1, wherein the composition comprises from 35% w/w to 45% w/w of pea protein, from 20% w/w to 40% w/w of alpha-glucooligosaccharide and from 20% w/w to 40% w/w of acacia gum, provided that the sum does not exceed 100%.

13. The method according to claim 1, wherein the composition comprises from 35% w/w to 45% w/w of pea protein, from 20% w/w to 40% w/w of alpha-glucooligosaccharide, from 20% w/w to 40% w/w of acacia gum, and from 2% w/w to 4% w/w of prednisolone, provided that the sum does not exceed 100%.

14. The method according to claim 1, wherein the composition is in the form of a pharmaceutical composition together with one or more pharmaceutically acceptable excipients and/or carriers; or in the form of a nutraceutical product.

15. The method according to claim 1, wherein the method comprises administering to the subject simultaneously, sequentially, or separately the composition and an antirheumatic drug.

16. The method according to claim 1, wherein the method comprises administering to the subject simultaneously, sequentially, or separately the composition and a corticosteroid.

17. The method according to claim 1, wherein the method comprises administering to the subject simultaneously, sequentially, or separately the composition and prednisolone.

18. The method according to claim 1, wherein the method is a method for treating autoimmune arthritis.

* * * * *